(12) United States Patent
Inagaki et al.

(10) Patent No.: US 6,997,878 B2
(45) Date of Patent: Feb. 14, 2006

(54) CUFF FOR BLOOD PRESSURE MONITOR

(75) Inventors: Takashi Inagaki, Kyoto (JP); Yoshihiko Sano, Kyoto (JP); Minoru Taniguchi, Kyoto (JP)

(73) Assignee: Omron Corporation, Kyoto (JP)

( * ) Notice: Subject to any disclaimer, the term of this patent is extended or adjusted under 35 U.S.C. 154(b) by 13 days.

(21) Appl. No.: 10/356,713

(22) Filed: Feb. 3, 2003

(65) Prior Publication Data

US 2003/0171683 A1    Sep. 11, 2003

Related U.S. Application Data

(63) Continuation-in-part of application No. 10/047,994, filed on Jan. 17, 2002, now Pat. No. 6,645,157.

(30) Foreign Application Priority Data

| Jan. 23, 2001 | (JP) | ................. 2001-13921 |
| Feb. 4, 2002 | (JP) | ................. 2002-26424 |

(51) Int. Cl.
*A61B 5/02* (2006.01)
(52) U.S. Cl. ..................... 600/499; 600/485
(58) Field of Classification Search ........ 600/485–507; 606/201–204, 204.15
See application file for complete search history.

(56) References Cited

U.S. PATENT DOCUMENTS

| 4,202,348 A | * | 5/1980 | Abe et al. ............... 600/493 |
| 4,572,205 A | | 2/1986 | Sjönell |
| 4,605,010 A | * | 8/1986 | McEwen ................. 600/499 |
| 4,979,953 A | * | 12/1990 | Spence .................. 606/202 |
| 5,201,758 A | * | 4/1993 | Glover ................... 606/202 |
| 5,454,831 A | * | 10/1995 | McEwen ................ 606/202 |
| 5,660,182 A | * | 8/1997 | Kuroshaki et al. ......... 600/499 |

FOREIGN PATENT DOCUMENTS

| JP | 60-37305 | 3/1985 |
| JP | 61-238229 | 10/1986 |
| JP | 2-1221 | 1/1990 |
| JP | 60-38931 | 2/1994 |

OTHER PUBLICATIONS

"Material". The American Heritage® Dictionary of the English Language (2003). http://www.xreferplus.com/entry4107342.*
"Normal". The American Heritage® Dictionary of the English Language (2003). http://www.xreferplus.com/entry/4113036.*
Webster's II new Riverside university dictionary, "density", 1994.*
Japanese Office Action dated Aug. 3, 2004 with English translation.

* cited by examiner

*Primary Examiner*—Robert L. Nasser
*Assistant Examiner*—Patricia Mallari
(74) *Attorney, Agent, or Firm*—Morrison & Foerster LLP

(57) ABSTRACT

The invention provides a variety of cuff design for blood pressure monitor, which assures an easy and firm fitting to an arm of a patient. Specifically, the curled elastic member of the cuff is overlapped at both end portions for easy fitting. The rigidity and thickness of the curled elastic member are designed to follow the shape of the upper arm of the patient, which significantly varies in size depending on the location of the arm.

6 Claims, 18 Drawing Sheets

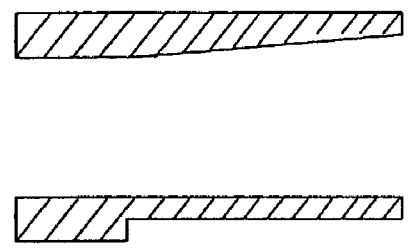
FIG. 7E
FIG. 7F
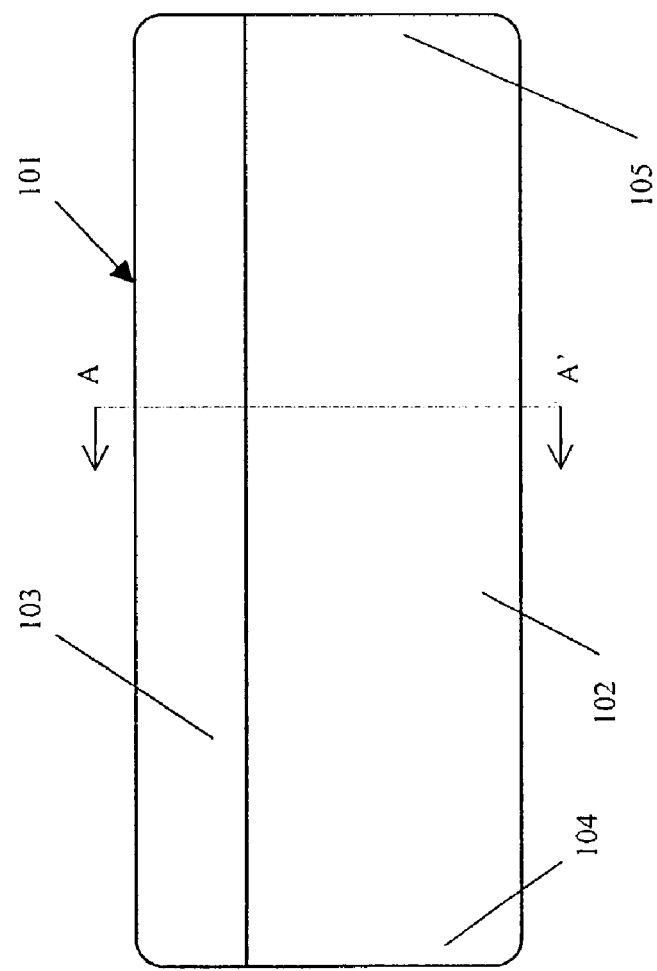
FIG. 7D

FIG.10A
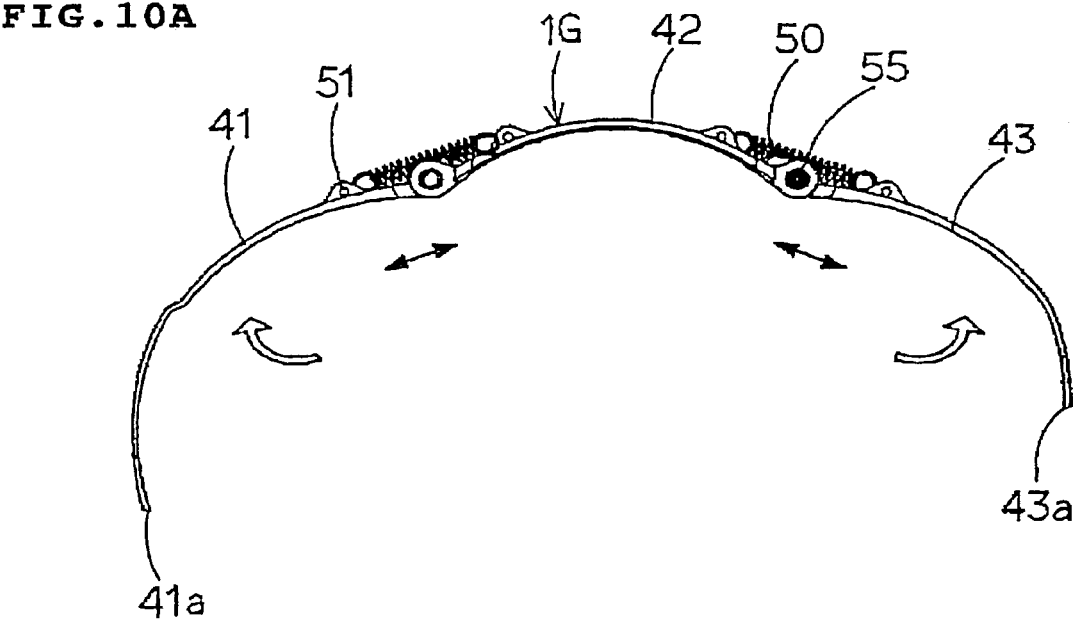
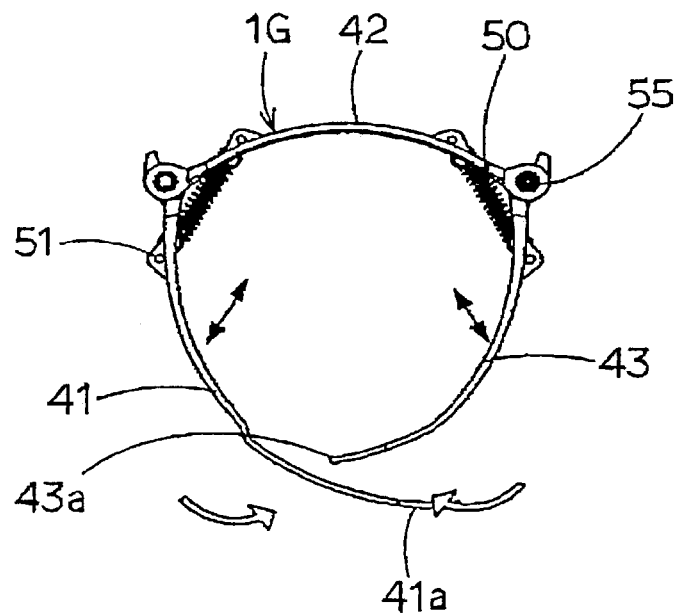
FIG.10B ly, in order to uncurl the curled elastic member 92, it has to be pulled with some strength. The user needs some experience to attach the elastic member 92 in the uncurled state onto his/her arm.

CUFF FOR BLOOD PRESSURE MONITOR

This application is a continuation-in-part of Ser. No. 10/047,994, filed Jan. 17, 2002, now U.S. Pat. No. 6,645,157.

BACKGROUND OF THE INVENTION

1. Field of the Invention

The present invention relates to a cuff for a blood pressure monitor and, more particularly, to a cuff characterized by a curled elastic member disposed on the outside of a bladder to hold a ring form of the cuff.

2. Description of the Related Art

As shown in FIG. 11 (perspective view) and FIG. 12 (sectional view), a cuff for a blood pressure monitor has generally a configuration such that a bladder 91 and a curled elastic member 92 are provided in a cloth bag 90. A tube 93 is connected to the bladder 91, and a velcro fastener 94 is attached on the outside of the cloth bag 90. The curled elastic member 92 is disposed on the outside of the bladder 91 to hold the cuff in a ring form by its elasticity. As shown in FIG. 13A, the curled elastic member 92 has an uniform thickness and has a sectional shape of a complete round in which a part thereof is a discontinuous portion 92a.

However, the curled elastic member 92 as shown in FIG. 13A has the following problems 1 to 3.

1. Operation of uncurling the curled elastic member 92 to be attached on an arm is not easy.

Since the sectional shape is a complete round, the curled elastic member 92 has to be uncurled and then attached on an arm. Specifically, in order to uncurl the curled elastic member 92, it has to be pulled with some strength. The user needs some experience to attach the elastic member 92 in the uncurled state onto his/her arm.

2. When the curled elastic member 92 is attached around an arm, the edges of the discontinuous portion 92a of the curled elastic member cut into the flesh of the arm due to its elastic force so that users in particular with thick arm often feel pain.

3. Since the curled elastic member 92 has uniform thickness and the sectional shape thereof is complete round, it cannot deform so as to correspond to a person with thick arm or a person with thin arm and hence is difficult to fit such arms.

For addressing the above described problems, Japanese Laid-open Patent Publication No. S61-238229 (1986) proposes a curled elastic member 92' as shown in FIG. 13B. This curled elastic member 92' is so configured that its thickness gradually increases in a circumferential direction of an arm from the both ends toward the center portion. Hence the rigidity of the curled elastic member 42 gradually increases. The thickness and rigidity are the maximum at the center portion.

This curled elastic member 92' has somewhat solved the aforementioned problems. However, for an arm whose diameter changes to a large extent depending on the part of the arm, in other words, for a largely-inclined arm, such as an upper arm whose diameter is small in the vicinity of the elbow but gradually increases toward the shoulder, the curled elastic member 92' fits the large diameter part of the arm while leaving a clearance with respect to the small diameter part of the arm. As described above, the curled elastic member 92' cannot sufficiently deform to correspond to the shape of the arm.

The present invention is directed to solving the above-mentioned problems associated with conventional cuffs for a blood pressure monitor. It is an object of the present invention to provide a cuff for a blood pressure monitor with excellent fitting ability which can fit various shapes of arms, in particular, largely-inclined arms.

SUMMARY OF THE INVENTION

The invention provides a cuff for a blood pressure monitor, which includes a bladder and a curled elastic member disposed on the outside of the bladder to hold a ring shape of the cuff. The curled elastic member has at least two different rigidities in an axial direction of the ring shape.

The cuff may be configured to be attached on an arm of a patient, and the curled elastic member may have a higher rigidity of the two different rigidities in a portion of the curled elastic member that is positioned at a thin portion of the arm when the cuff is attached on the arm, and may have a lower rigidity of the two different rigidities in a portion of the curled elastic member that is positioned at a thick portion of the arm when the cuff is attached on the arm.

BRIEF DESCRIPTION OF THE DRAWINGS

FIGS. 7C–7F are a perspective view, an exploded view and two cross-sectional view, respectively, of a modification of the embodiment of FIGS. 7A and 7B;

FIGS. 10A and 10B are side views of the curled elastic member in an uncurled state and in a curled state, respectively;

DETAILED DESCRIPTION OF THE INVENTION

Figure 11:
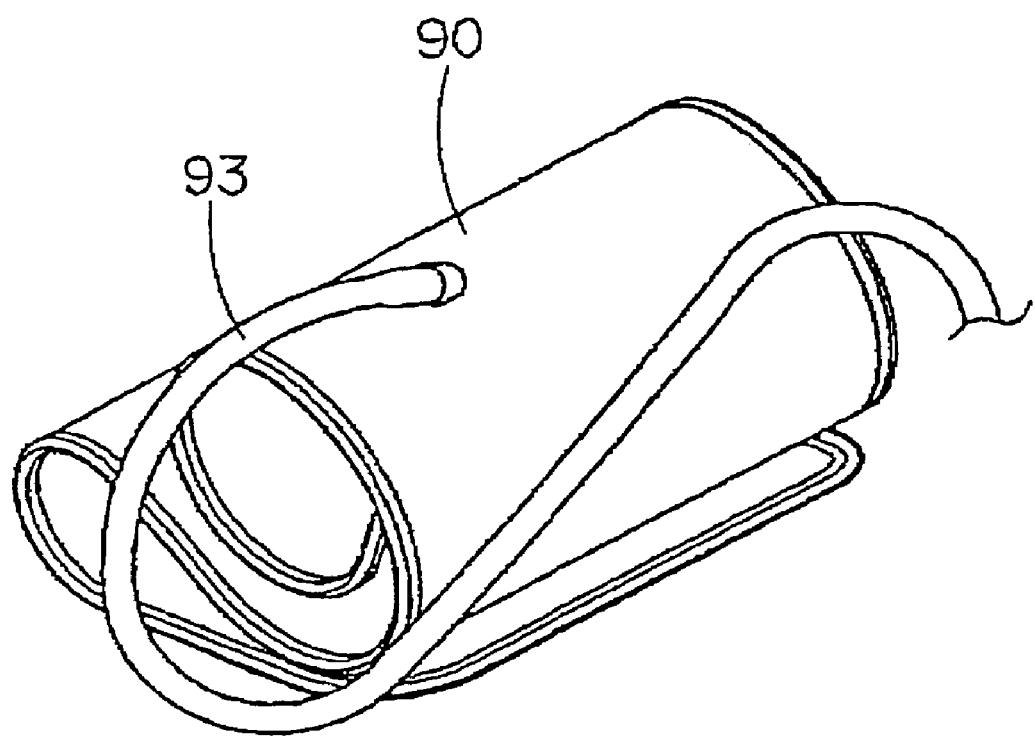
FIG. 11 is a perspective view showing a general cuff.
Figure 12:
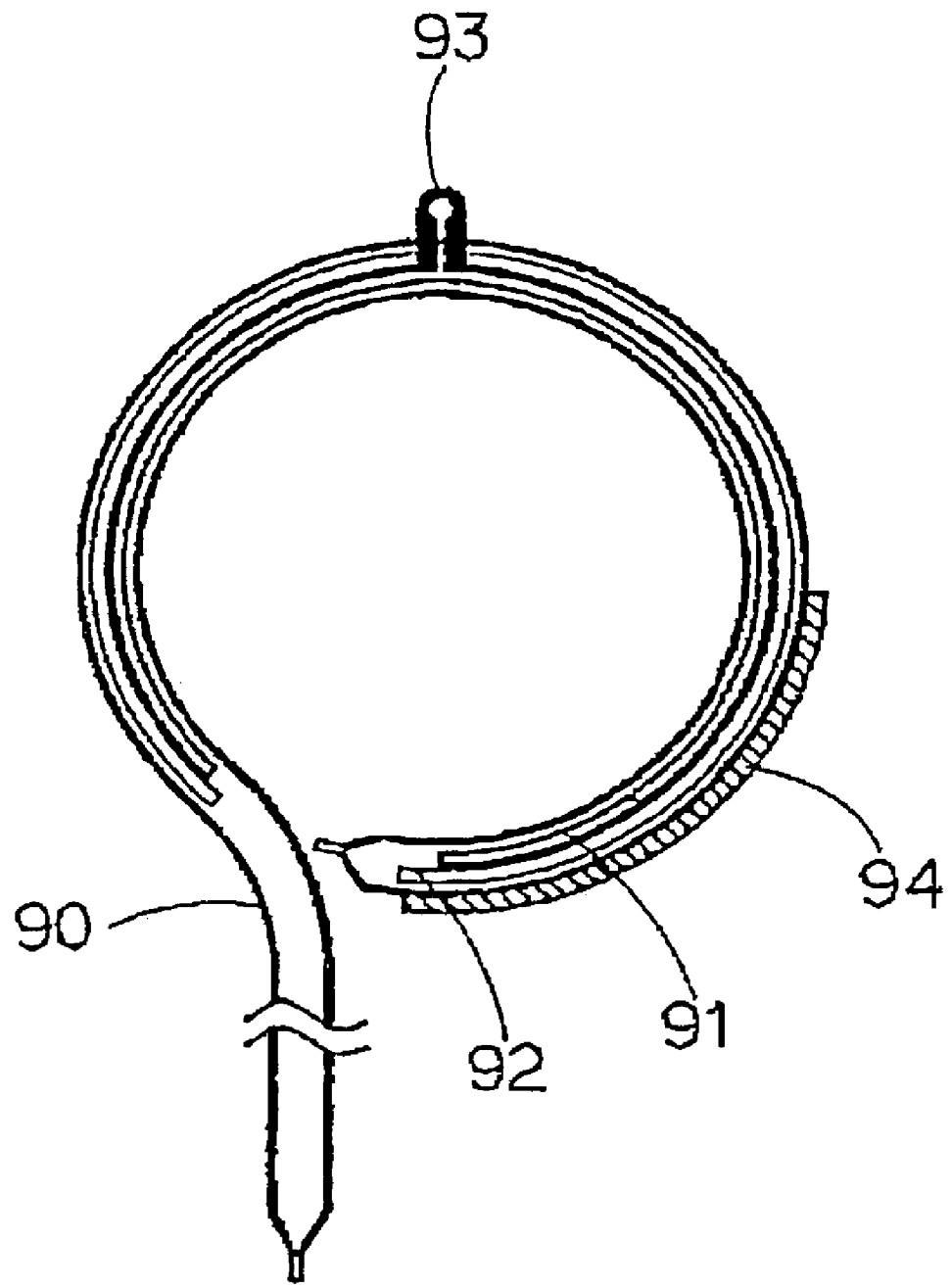
FIG. 12 is a sectional view showing the inside of the cuff of FIG. 11.
Figure 13A:
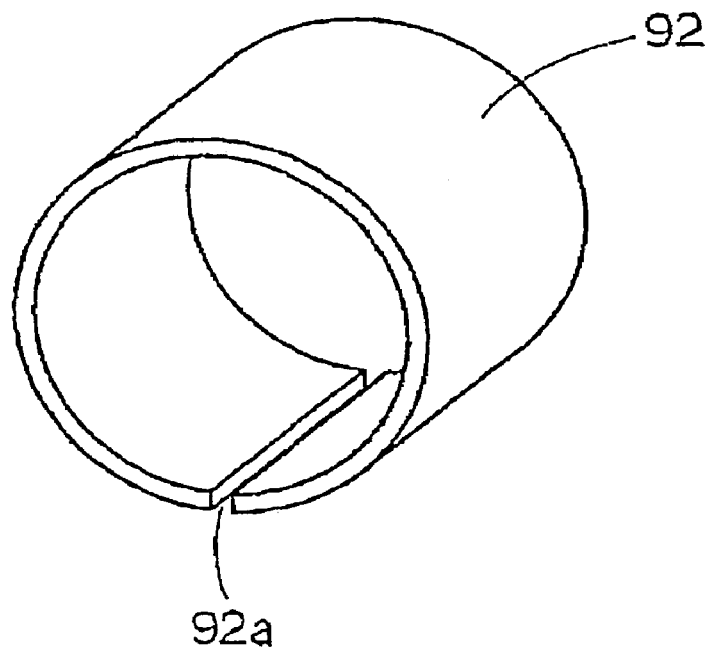
FIG. 13A is a perspective view of a curled elastic member according to a conventional technique, disposed in the cuff of FIG. 11
Figure 13B:
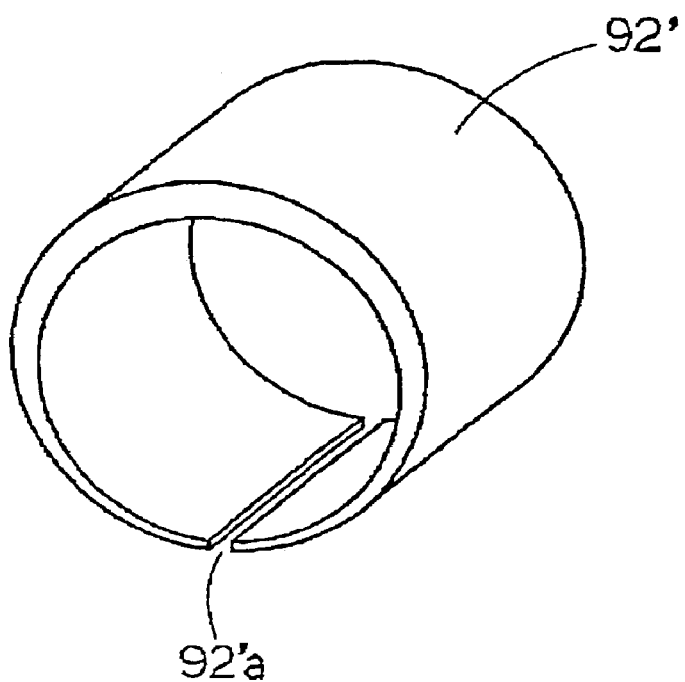
FIG. 13B is a perspective view of a curled elastic member according to another conventional technique.

The present invention will be described below on the basis of embodiments. It is to be noted that the cuff for a blood pressure monitor in the present invention has its feature in a curled elastic member thereof, and structural features and its operation of the cuff except the curled elastic member may be those of conventional cuffs shown in FIG. 11. Accordingly, the following explanation focuses on the curled elastic member.

Figure 1A:
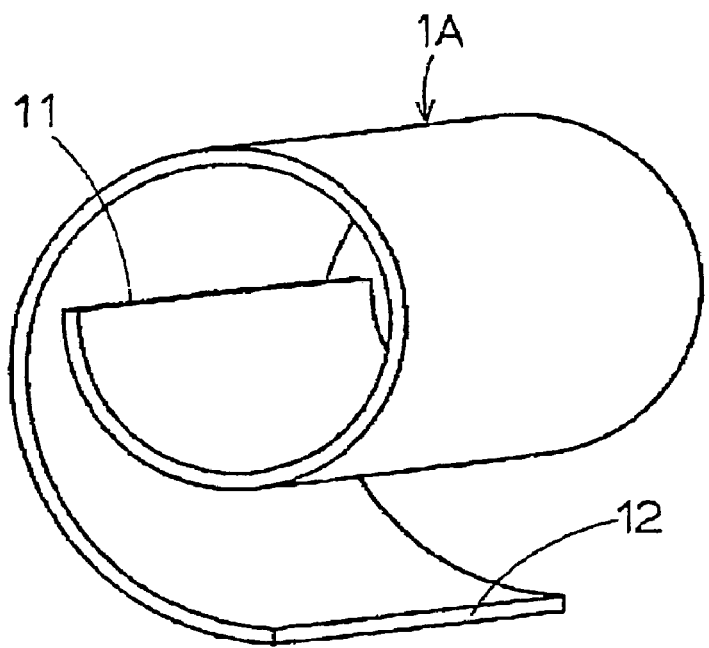
FIG. 1A is a perspective view of a curled elastic member according to an embodiment, provided for a cuff for a blood pressure monitor.
Figure 1B:
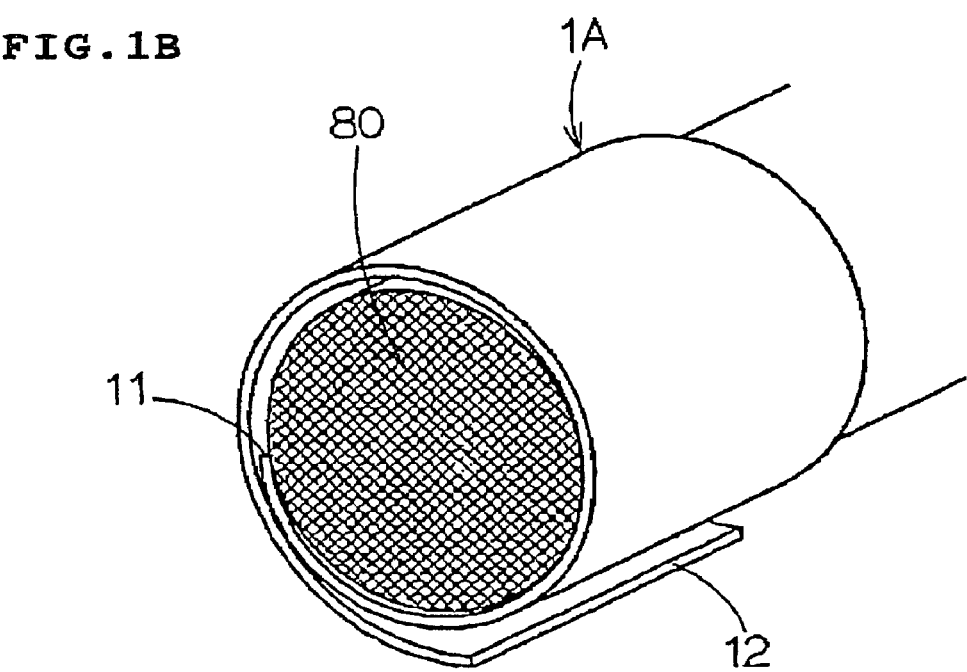
FIG. 1B is a perspective view showing a state where the curled elastic member is attached on an arm.

FIG. 1A is a perspective view of a curled elastic member, according to an embodiment, provided for a cuff for a blood pressure monitor, and FIG. 1B is a perspective view when the curled elastic member is attached to an arm. One end 12 of this curled elastic member 1A is extended outward so as to enwind the other end 11 inward. That is, from the other end 11 to the mid portion of the curled elastic member where the other end 11 meets the curled elastic member, the radius of curvature of the curled elastic member gently increases. From the mid portion of the curled elastic member to the one end 12, the radius of curvature largely increases.

Figure 2A:
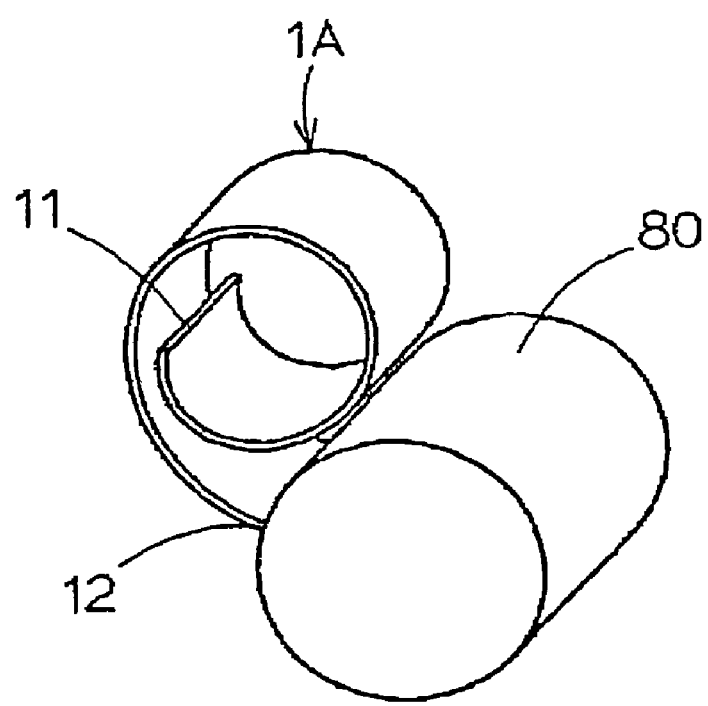
FIGS. 2A and 2B are perspective views showing a first step and a second step, respectively, of attaching the curled elastic member of FIGS. 1A and 1B onto an arm.
Figure 2B:
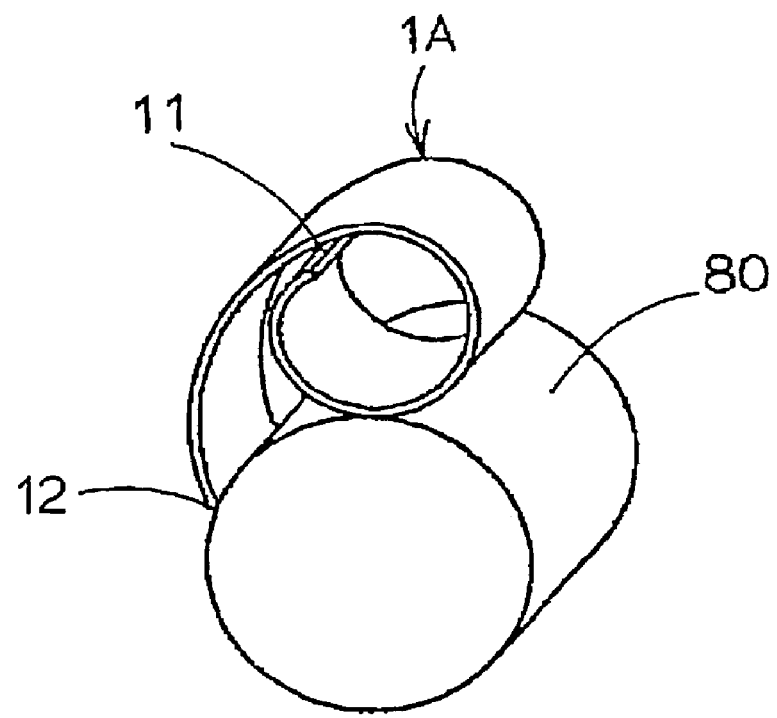
Figure 3A:
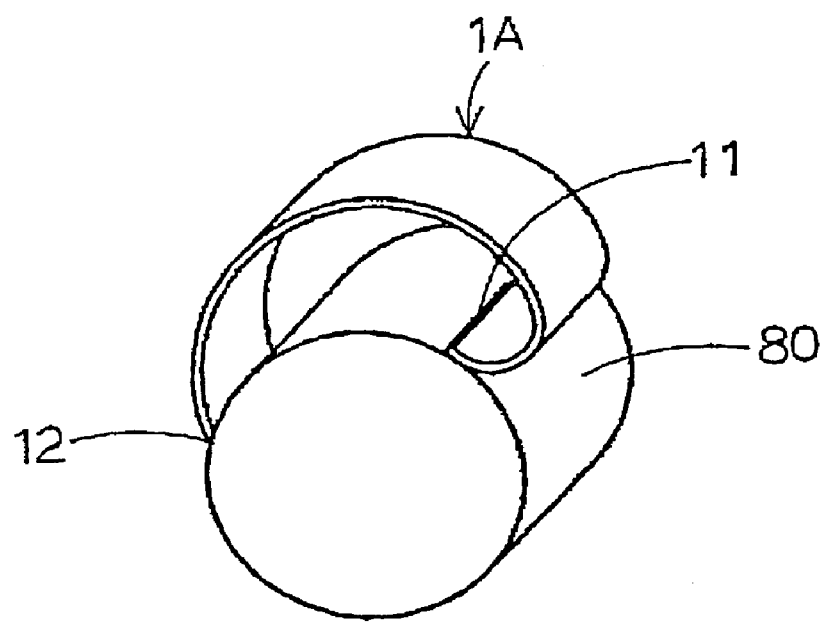
FIG. 3A is a perspective view showing a third step of attaching the curled elastic member of FIGS. 1A and 1B onto an arm.
Figure 3B:
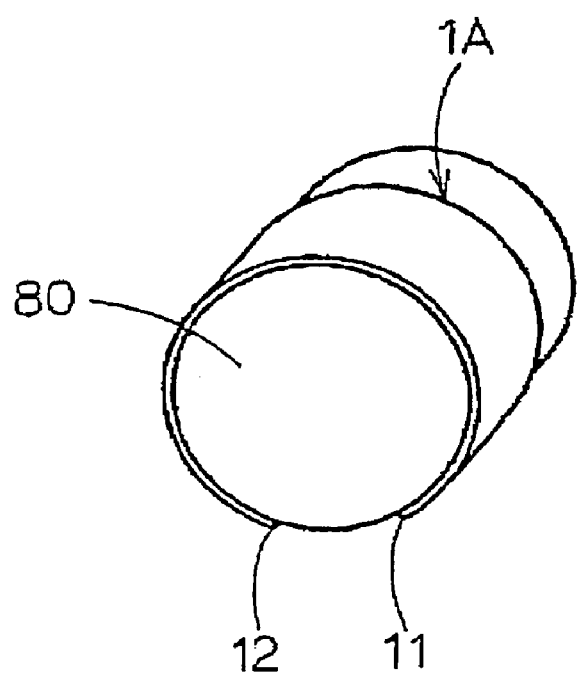
FIG. 3B is a perspective view showing an attached state.

A method of attaching the curled elastic member 1A around an arm 80 will be described by referring to FIGS. 2A and 2B and FIGS. 3A and 3B. First, in FIG. 2A, the one end portion 12 as a longer one of the curved elastic member 1A is thrown over the arm 80. In this state, while uncurling the curled elastic member 1A, it is pulled to the side opposite to the one end portion 12 (FIG. 2B). The curled elastic member 1A is further pulled until the width of the uncurled width becomes about equal to that of the arm 80 (FIG. 3A), the curled elastic member 1A is put on the arm 80 (FIG. 3B). The curled elastic member 1A is then fit to the arm 80 by its elasticity. In such a manner, the curled elastic member 1A, i.e., the cuff is attached on the arm.

When the curled elastic member 1A is used, the operation of uncurling the curled elastic member 1A and the operation of attaching the curled elastic member 1A onto the arm 80 can be simultaneously performed, so that the operation of attaching the curled elastic member 1A onto the arm 80 is easy. Since the one end portion 12 is longer than the other end portion 11 and the other end portion 11 is enwinded inward, when the curled elastic member 1A is attached on the arm 80, the other end portion 11 and the one end portion 12 do not easily cut into the arm 80, and the subject does not feel pain.

Figure 4A:
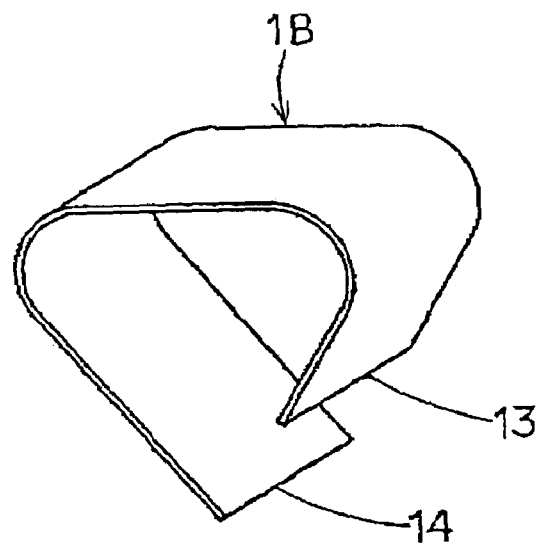
FIG. 4A is a perspective view of a curled elastic member according to another embodiment.

FIG. 4A is a perspective view of a curled elastic member according to another embodiment. This curled elastic member 1B has a sectional shape of approximately triangle and has an extended one end portion 14. The curled elastic member 1B can be attached onto the arm 80 in a manner similar to the above-mentioned curled elastic member 1A. That is, the one end portion 14 which is the longer one of the curled elastic member 1B is thrown over the arm 80, the curled elastic member 1B is pulled to be uncurled and put on the arm 80. Consequently, the operation of uncurling the curled elastic member 1B and the operation of attaching the curled elastic member 1B on the arm 80 can be simultaneously performed.

Figure 4B:
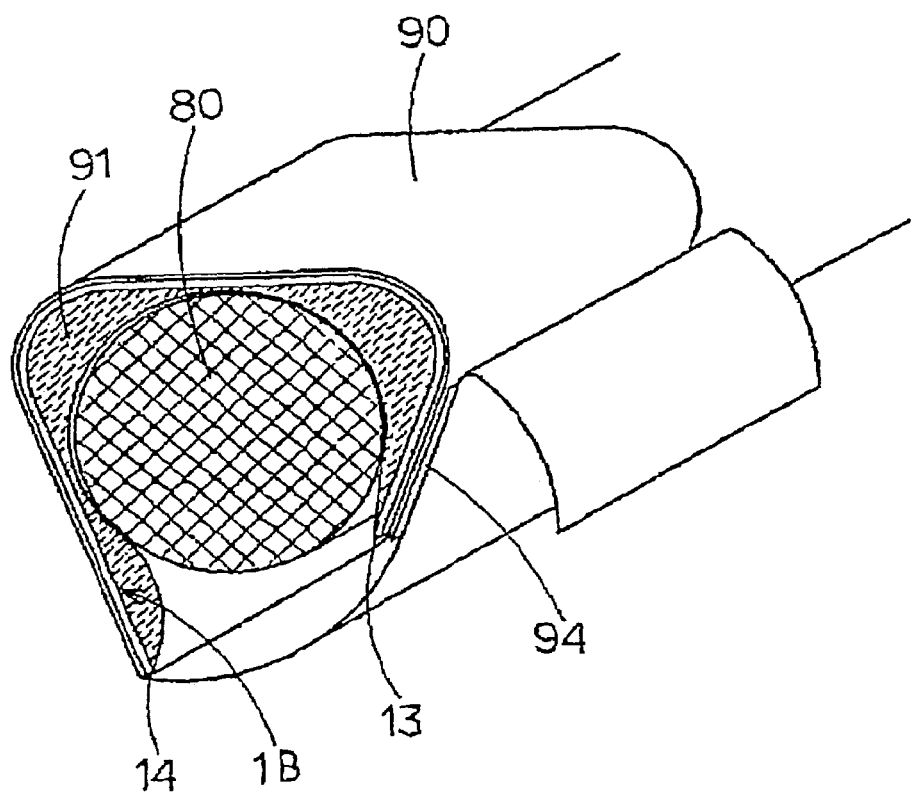
FIG. 4B is a perspective view showing a state where a cuff having the curled elastic member is attached on an arm.

When the curled elastic member 1B whose sectional shape is approximately triangle is attached on the arm 80, as shown in FIG. 4B, a gap is formed between each of the corners and the arm 80. However, the bladder 91 is inflated so as to fill the gap by injection of air, so that the action of pressing the arm 80 with the bladder 91 is not hindered. The sectional shape of the curled elastic member 1B may be, besides approximately triangle, quadrangle or polygon.

Figure 5A:
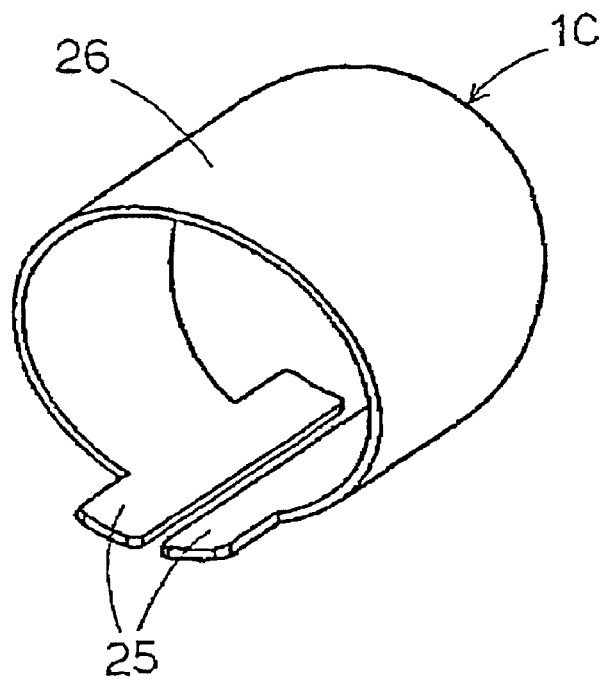
FIGS. 5A and 5B are a perspective view and an exploded view, respectively, of a curled elastic member according to further another embodiment.
Figure 5B:
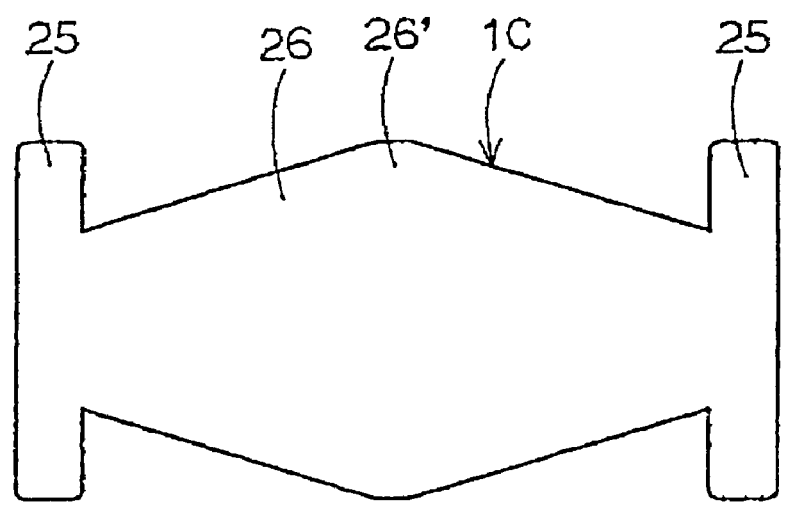

FIGS. 5A and 5B are a perspective view and an exploded view, respectively, of a curled elastic member according to further another embodiment. This curled elastic member 1C has a narrow portion 26 in which a width in the axial direction of an arm is partly narrowed between a center portion 26' in the circumferential direction of the arm and both end portions 25. The narrow portion 26 has a width gradually decreased from the center portion 26' towards the both end portions 25. In the curled elastic member 1C, the rigidity of the narrow portion 26 is reduced. Thus, the curled elastic member 1C (i.e., a cuff) gets easily to be twisted, so that it easily fits to an arm of any shape such as a straight arm or tapered arm.

Since the both end portions 25 of the curled elastic member 1C are not formed as the narrow portion 26, the rigidity of the both end portions 25 does not deteriorate, and the arm can be securely held by the both end portions 25. Further, by not making the both end portions 25 as the narrow portion 26, as compared with a case where the both end portions 25 are also formed as the narrow portion 26, the subject does not have strange feeling such that the both end portions 25 cut into the flesh of the arm.

Figure 6A:
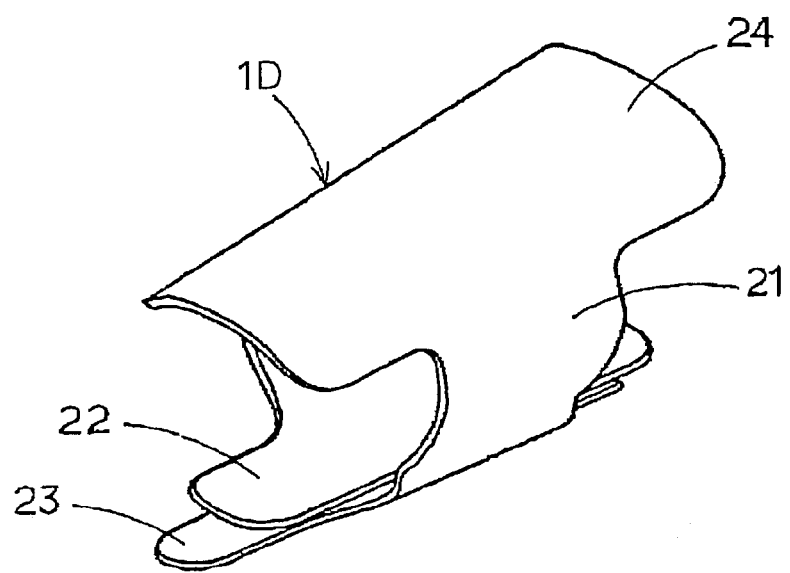
FIGS. 6A and 6B are a perspective view and an exploded view, respectively, of a curled elastic member according to further another embodiment.
Figure 6B:
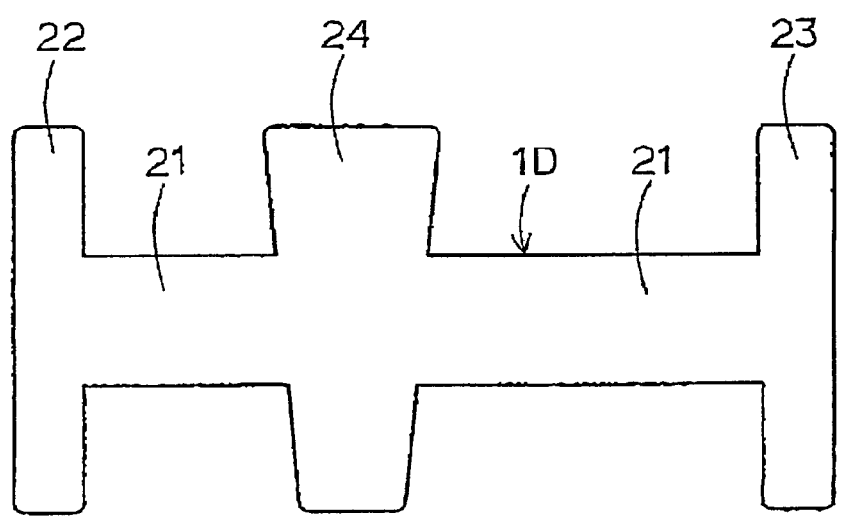

FIGS. 6A and 6B are a perspective view and an exploded view, respectively, of a curled elastic member according to further another embodiment. This curled elastic member 1D has a narrow portion 21 in which a width in the axial direction of an arm is partly narrowed between an approximately center portion 24 in the circumferential direction of the arm and both end portions 22 and 23. The narrow portion 21 has a fixed width in the circumferential direction of the arm. The approximately center portion 24 does not have a fixed width but is tapered in correspondence with an arm which is generally tapered from the shoulder side toward the elbow side. Therefore, at the time of attachment onto an arm, the wider side of the center portion 24 has to be set on the shoulder side. The user has to see the direction of the curled elastic member 1D when it is set in the cloth bag 90 of the cuff. Further, one end portion 23 is extended outward so as to enwind the other end portion 22 inward.

In the curled elastic member 1D, in a manner similar to the curled elastic member 1C, the rigidity of the narrow portion 21 is reduced. Consequently, the curled elastic member 1D (i.e., the cuff) gets easily to be twisted, so that it easily fits to an arm of any shape such as a straight arm or tapered arm.

Since the both end portions 22 and 23 of the curled elastic member 1D are not formed as the narrow portion 21, the rigidity of the both end portions 22 and 23 does not deteriorate, and the arm can be securely held by the both end portions 22 and 23. Further, by not making the both end portions 22 and 23 as the narrow portion 21, as compared with a case such that the both end portions 22 and 23 are also formed as the narrow portion 21, the subject does not feel strange such that the both end portions 22 and 23 cut into the flesh of the arm. Obviously, at the time of attachment to an arm, the one end portion 23 which is the longer one is thrown over the arm.

Figure 7A:
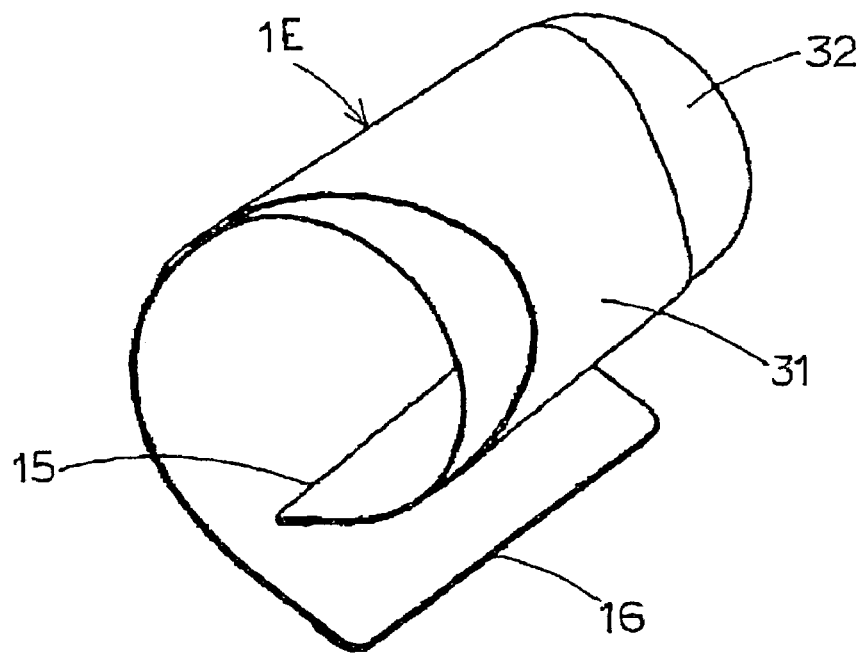
FIGS. 7A and 7B are a perspective view and an exploded view, respectively, of a curled elastic member according to further another embodiment.
Figure 7B:
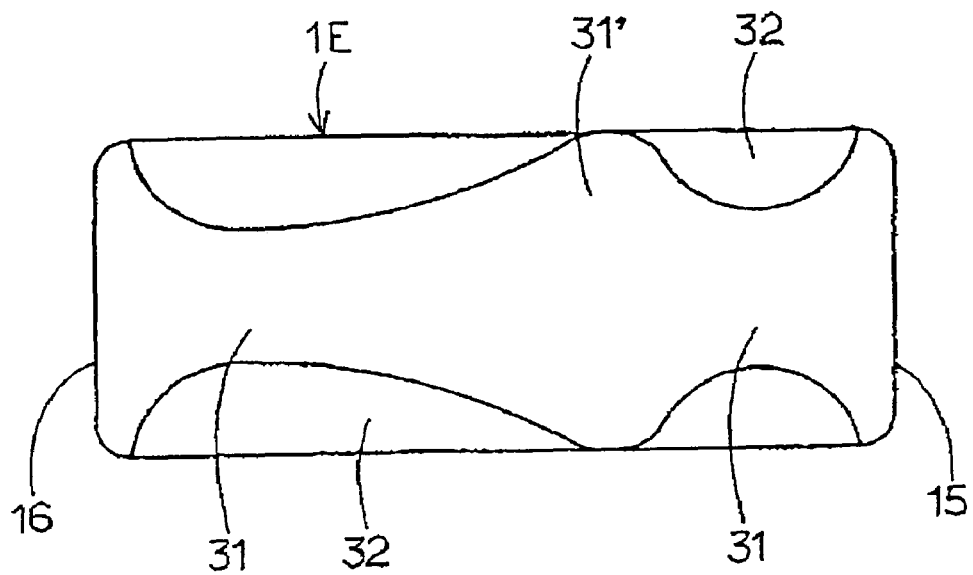

FIGS. 7A and 7B are a perspective view and an exploded view, respectively, of a curled elastic member according to further another embodiment. This curled elastic member 1E has a narrow portion 31 in which a width in the axial direction of the ring shape of the cuff is partly narrowed between an approximately center portion 31' in the circumferential direction of the ring shape of the cuff and both end portions 15 and 16. A thin portion 32 which is thinner than the narrow portion 31 is provided at the remainder of the curled elastic member. The narrow portion 31 has a width which gently increases and decreases from the end portions 15 and 16 toward the center portion 31'. The thin portion 32 and the narrow portion 31 provide a substantially rectangular elastic member when it is uncurled. Consequently, the curled elastic member 1E as a whole has a fixed width. The one end portion 16 is extended outward so that the other end portion 15 is enwinded inward.

In order to provide the thin portion 32, for example, the thin portion 32 as a separate member may be joined to the narrow portion 31 or the portion 32 other than the narrow portion 31 may be formed thin by cutting, integral molding or the like at the time of making the whole curled elastic member 1E. The planar shape pattern of the narrow portion 31 is not limited to that shown in the drawing but, for example, the pattern of the narrow portion 21 in the curled elastic member 1D in FIG. 6 may be used.

The curled elastic member 1E is obtained by improving the curled elastic member 1D. That is, in the case of the form where the portion missed by the narrow portion 31 exists, when the bladder is inflated, it is feared that the bladder is inflated from the side (missing portion) of the narrow portion 31 to the surface side of the cuff so that the arm cannot be sufficiently pressed, and there is also the possibility such that, in a process of taking blood pressure data while changing air pressure, noise occurs due to inflation from the missing portion to the outside of the bladder, so that there is the possibility that blood pressure cannot be measured stably.

However, by forming the missing portion generated due to the narrow portion 31 as the thin portion 32, while maintaining the effects of the curled elastic member 1D, the possibilities of the above-mentioned problems can be also eliminated. That is, by forming the curled elastic member 1D so as to be fit to any of arms of various shapes by the both end portions and so as to be easily twisted, an effect such that the curled elastic member can be easily fit to an arm of any shape such as a straight arm or tapered arm is obtained.

Figure 7C:
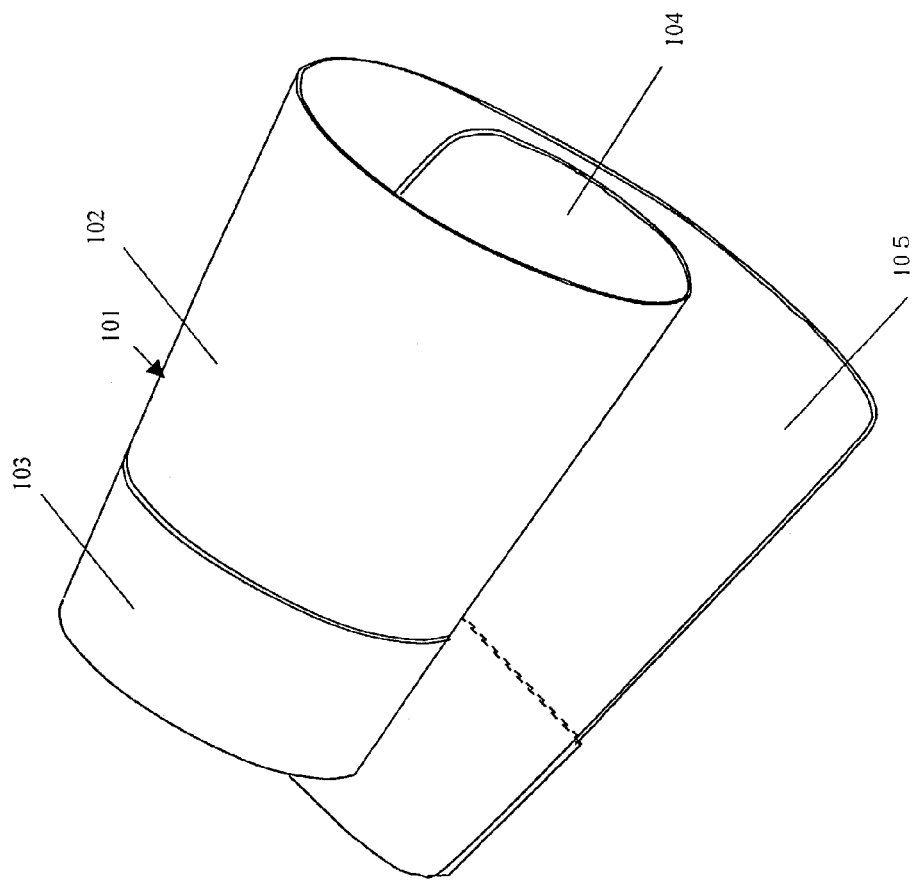

FIGS. 7C and 7D are a perspective view and an exploded view of a curled elastic member provided for a cuff for a blood pressure monitor, according to the first modification of the embodiment of FIGS. 7A and 7B. A section view viewed from the right direction along the line A–A' of FIG. 7D is shown in FIG. 7E. A curled elastic member 101 is formed of a resin such as PP (polypropylene), and includes two regions having different thicknesses, i.e., a thin portion 102 and a thick portion 103. When the curled elastic member 101 is attached around an arm, it is wounded so that one end portion 104 is placed inside another end portion 105. Attention is now directed to an axial direction of the ring shape of the cuff, or the direction of an arm when the curled elastic member 101 is attached on the arm. It can be seen that one end of the cylindrically wound curled elastic member 101 forms the thin portion 102 and the other end forms the thick portion 103. The thick portion 103 has high rigidity so that it can firmly grip the arm, whereas the thin portion 102 has low rigidity so that it can easily deform in conformance with the shape of the arm in contrast to the thick portion 103. Consequently, when the curled elastic member 101 is oriented so that the thick portion 103 corresponds to the arm part of small diameter and the thin portion 102 corresponds to the arm part of large diameter, and the curled elastic member 101 is wound so that no clearance is left between the thick portion 103 and the arm part of small diameter, the thin portion 102 deforms to closely follow the shape of the arm part of large diameter. As a result, it can be attached around the entire circumference of the arm without leaving any clearance.

In the first modification, the rigidity of the curled elastic member 101 is varied in two steps. However, the curled elastic member may have more than two rigidities, or may change the rigidity continuously by, for example, gradually changing the thickness in the axial direction of ring shape of the cuff from the one end side to the other end side as shown in FIG. 7F.

Figure 7G:
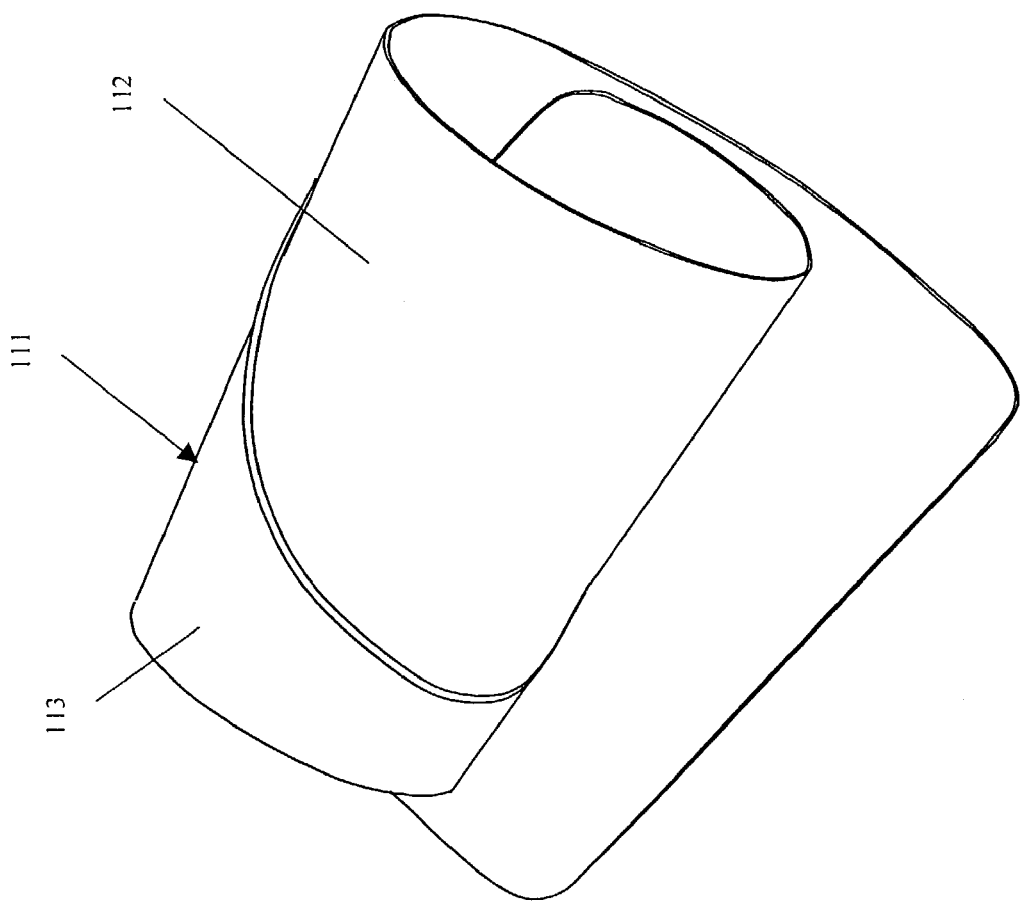
FIGS. 7G–7I are a perspective view, an exploded view and a cross-sectional view, respectively, of another modification of the embodiment of FIGS. 7A and 7B.
Figure 7I:
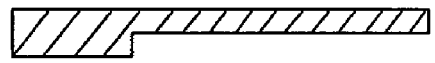
Figure 7H:
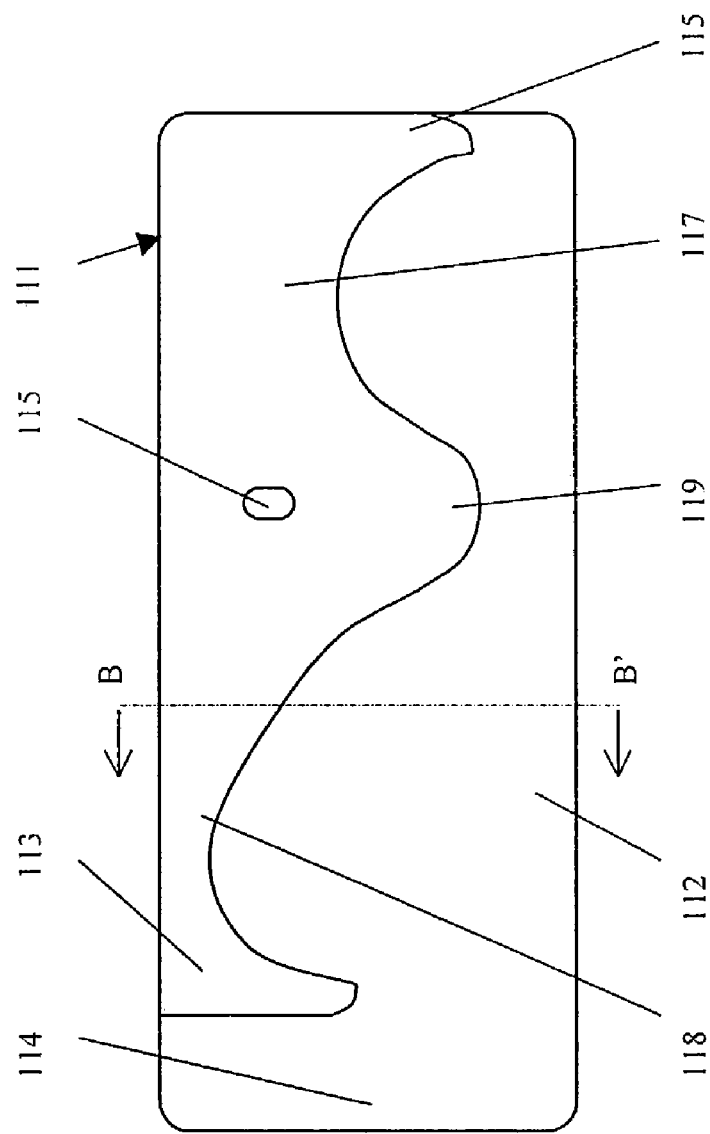

FIGS. 7G and 7H are a perspective view and an exploded view showing a curled elastic member provided for a cuff for a blood pressure monitor, according to the second modification of the embodiment of FIGS. 7A and 7B. A section view viewed from the right direction along the line B–B' of FIG. 7H is shown in FIG. 7I. A curled elastic member 111 includes two regions having different thickness, i.e., a thin portion 112 and a thick portion 113. When the curled elastic member 111 is attached around an upper arm, it is wounded so that the thin portion 112 is located on the shoulder side and one end portion 114 is placed inside another end portion 115. Attention is now directed to an axial direction of the ring shape of the cuff, or the direction of an arm when the curled elastic member 111 is attached on the arm. It can be seen that the part corresponding to the shoulder side forms the thin portion 112 and the part corresponding to the elbow side forms the thick portion 113. Accordingly, as is the case with the first modification, when the thick portion 113 having high rigidity is wound around the arm part near the elbow where the diameter is smaller than that of the part on the shoulder side so as not to leave a clearance, the thin portion 112 having a lower rigidity deforms to closely follow the shape of the arm part on the shoulder side where the diameter is larger than that of the elbow side. As a result, it can be attached around a largely-inclined arm without leaving any clearance.

Next, attention is directed to a circumferential direction the ring shape of the cuff, or the direction around the arm when the curled elastic member 101 is attached on the arm. It can be seen that on either side of a hole 116, through which a tube connected to a bladder (not shown) is to be inserted into the curled elastic member 111, is provided a narrow portion 117, 118 where the width of the thick portion 113 along the axial direction of is partially narrowed. These narrow portions 117, 118 can conform to arms having various inclination angles and enables attachment while ensuring higher fitting ability since the rigidity along the axial direction of the curled elastic member 111 is low in these narrow portions 117, 118 and hence the curled elastic member 111 can easily twist.

Furthermore, in the vicinity of the hole 116 is formed a wide portion 119 where the width of the thick portion 113 along the axial direction is larger than those of the thin portions, whereby the rigidity is set higher so as to reduce the deformation during application of pressure to the arm by the bladder. Furthermore, the curled elastic member has two different end portions, i.e., one end portion 114 and the other end portion 115. The one end portion 114 and its vicinity are formed as the thin portion 112, and the other end 115 and its vicinity are formed as the thick portion 113. When the cured elastic member is wound around an upper arm, the one end portion 114, which is designed to be wound inside and come into contact with the arm, will conform to the shape of the arm to reduce the pain of the subject for blood pressure measurement since it has a low rigidity. The other end potion 15 will ensure close attachment to the arm since it has high rigidity.

In order to form a curled elastic member having non-uniform rigidity, for example, the thin portion 112 and the thick portion 113 may be integrally formed to make the curled elastic member 111 or the part corresponding to the thin portion 112 may be formed by cutting from a member having the entire shape of the curled elastic member 111 and having the thickness of the thick portion 113. Also, a member having a shape of the part corresponding to the thick portion 113 may be bonded on a member having the entire shape of the curled elastic member 111 formed in a thickness of the thin portion 112. In this configuration, it is effective to use materials of different rigidities such that the member having the entire shape is formed of a material of low rigidity and the member having a shape of the part corresponding to the thick portion 113 is formed of a material of high rigidity, for example.

The pattern of the thin portion 112 and the thick portion 113 shown in FIG. 7H does not limit the pattern design used in this embodiment.

Figure 7J:
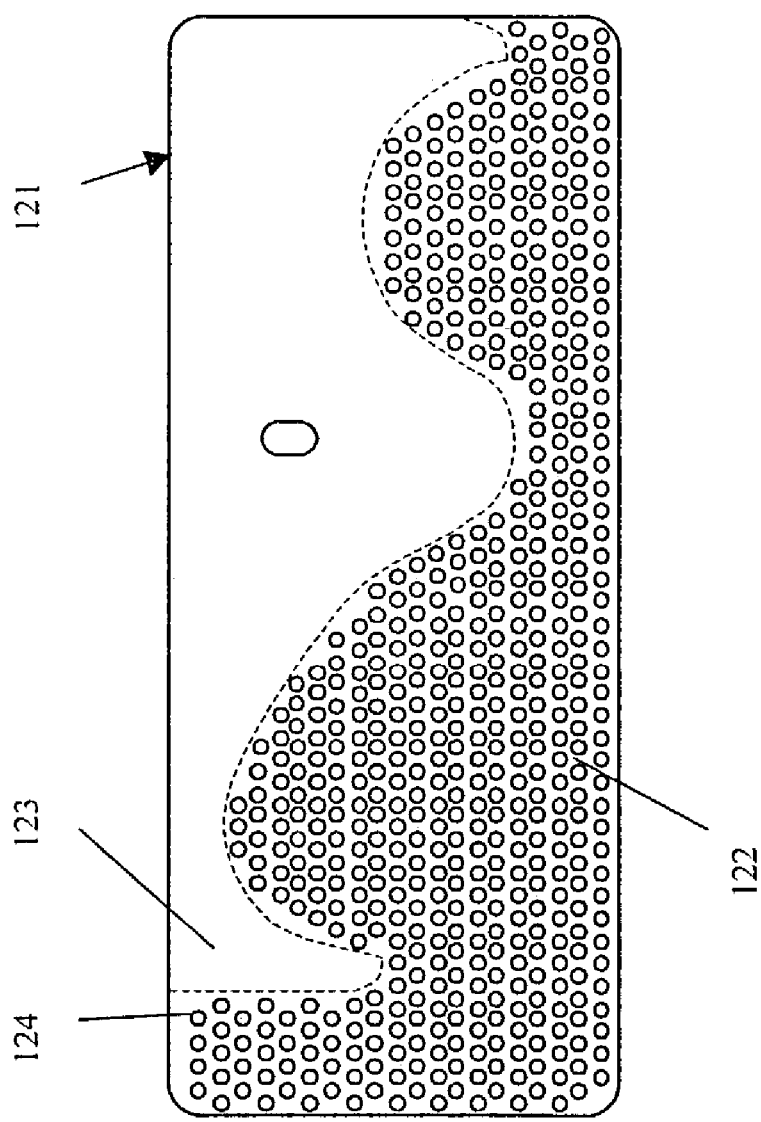
FIG. 7J is a schematic exploded view of a modification of the curled elastic member of FIGS. 7G–7I.

FIG. 7J shows an exploded view showing a curled elastic member 121 provided for a cuff for a blood pressure monitor, according to a further modification of the second modification of the embodiment of FIGS. 7A and 7B. In this configuration, the rigidities along the axial and circumferential directions of the ring shape of the cuff are changed by effecting a punching (boring) process on the material. Specifically, a part 122 which is intended to have a low rigidity corresponding to the thin portion 112 in the curled elastic member 111 of the second modification is subjected to a punching (boring) process to provide a plurality of holes (or bores) 124, while a part 123 which is intended to have a high rigidity corresponding to the thick part 113 is subjected to neither punching nor boring process. As a result, the entire thickness of the curled elastic member 121 is uniform, while the rigidity is not uniform in the axial and circumferential directions, which allows desired rigidity distribution for conforming to the shape of the arm. Accordingly, as is the case with the second modification, the curled elastic member 121 can be closely attached around any arms having a variety of shapes and degrees of inclination.

The positions, size and population of the holes may be adjusted to provide more effective attaching characteristics of the curled elastic member. For example, the size of the bore or hole is not necessarily identical among them, but large and small bores or holes may exist together. Although either punching or boring process is effected in this embodiment, processes for making holes and bores may be effected in combination.

Figure 8A:
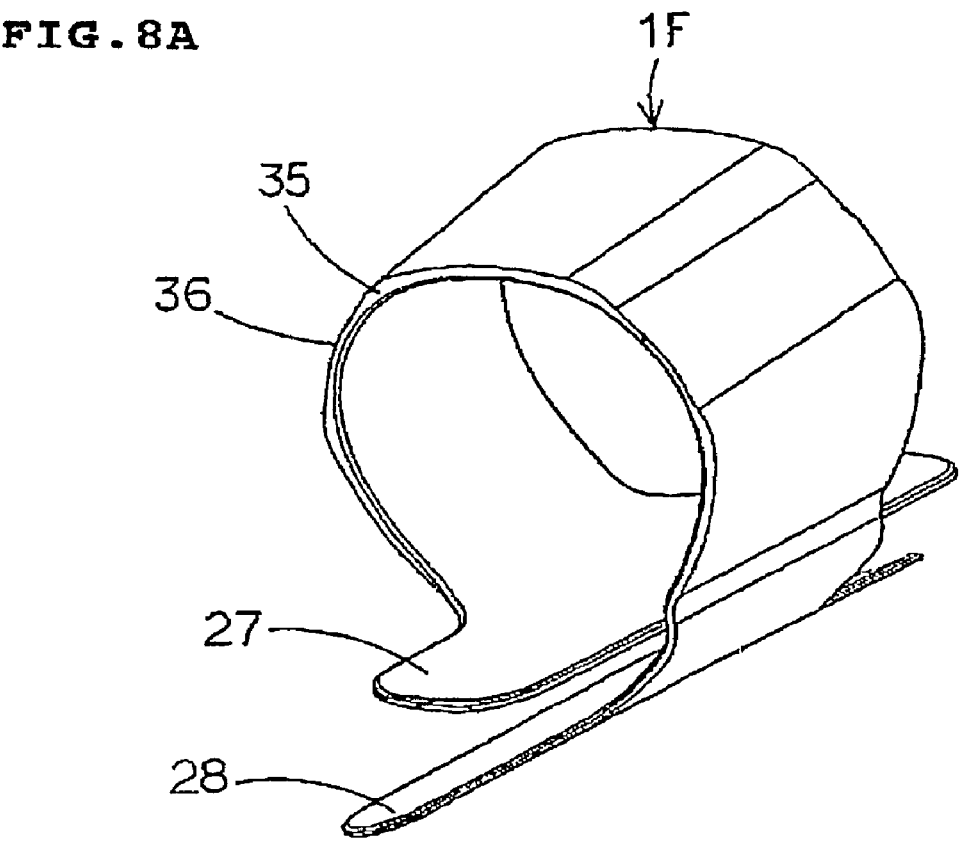
FIGS. 8A and 8B are a perspective view and a sectional view, respectively, of a curled elastic member according to further another embodiment.
Figure 8B:
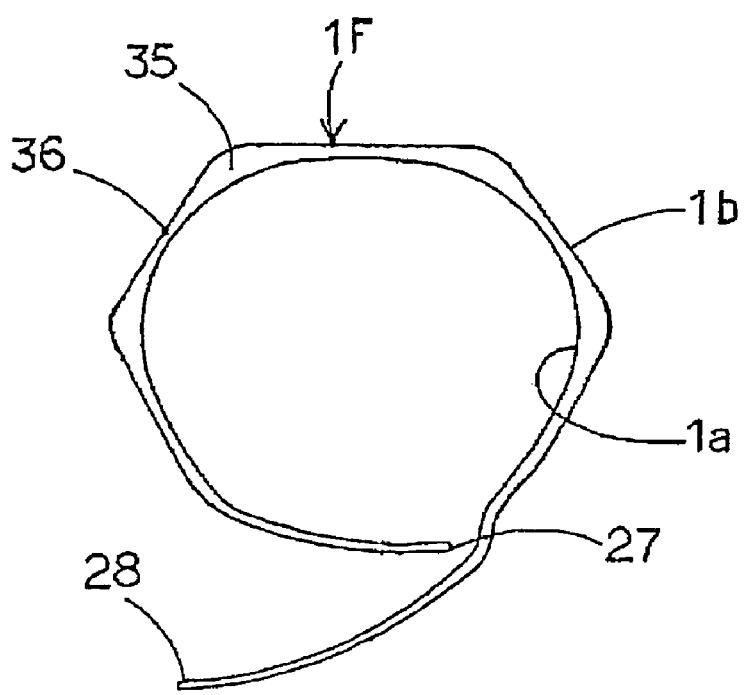

FIGS. 8A and 8B are a perspective view and a sectional view of a curled elastic member according to further another embodiment. This curled elastic member 1F is formed so that its inner circumferential face 1a is an approximately round shape and an outer circumferential face 1b has a polygon shape (approximately hexagon herein). With the structure, the corner portions of the polygon become thick portions 35 and the side portions become thin portions 36. Therefore, the form in which the thickness is changed is obtained as a result. Particularly, in a manner similar to the curled elastic members 1C to 1E, the shape can be altered according to variations in the arm, and the curled elastic member does not easily cut in the arm and fits the arm very well. Obviously, since the one end portion 28 is extended outward than the other end portion 27, the curled elastic member is easily attached on the arm.

Figure 9:
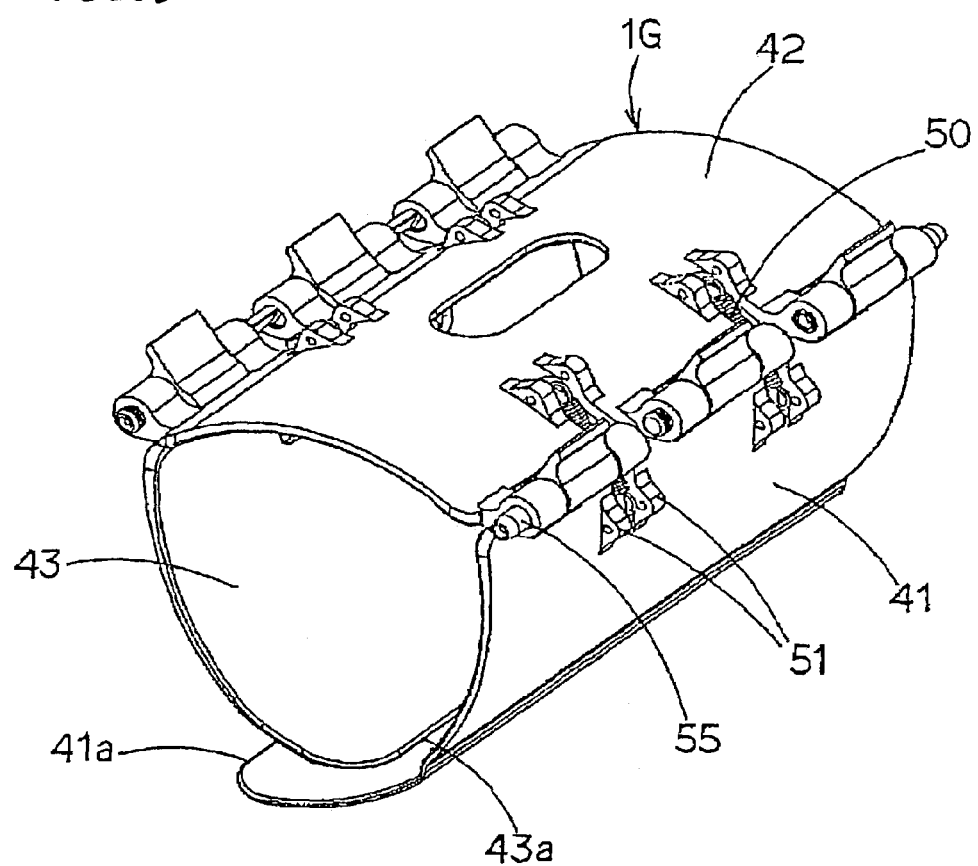
FIG. 9 is a perspective view of a curled elastic member according to further another embodiment.

FIG. 9 is a perspective view of a curled elastic member according to further another embodiment. FIGS. 10A and 10B are side views of the curled elastic member in an uncurled state and in a curled state, respectively. This curled elastic member 1G is formed by connecting a plurality of (three herein) elastic pieces 41, 42, and 43 by hinges. Two coil springs 50 as energizing means are attached to the respective hinged portions. The elastic pieces 41 and 43 serve as both end portions, and the elastic piece 42 serves as a center portion. The elastic piece 41 is set longer than the elastic piece 43 so that an end 43a of the elastic piece 43 is enwinded inward.

Three hinges as the hinged portions are provided between the elastic pieces 41 and 42, and between the elastic pieces 42 and 43. The elastic pieces 41 to 43 can relatively swing around a spindle 55 of each hinged portion as a fulcrum. The coil springs 50 are attached to supporting portions 51 provided at facing ends of the elastic pieces 41 to 43. In each of the elastic pieces 41 to 43, a notch (to which no reference numeral is designated) for receiving the coil spring 50 is formed.

When the curled elastic member 1G is uncurled by a predetermined angle or more, the coil spring 50 is energized in the direction of uncurling the curled elastic member 1G. When the curled elastic member 1G is curled by a predetermined angle or less, the coil spring 50 is energized in the direction of curling the curled elastic member 1G. That is, as obvious from FIGS. 10A and 10B, when the coil spring 50 is positioned on the outer side than the spindle 55 as a fulcrum of each of the elastic pieces 41 to 43, the energizing force acts in the direction of uncurling the curled elastic member 1G (FIG. 10A). When the coil spring 50 is positioned on the inner side than the spindle 55, the energizing force acts in the direction of curling the elastic member 1G (FIG. 10B). However, the curled elastic member 1G is usually in the closed state as shown in FIG. 10B.

When the curled elastic member 1G is attached on an arm, the end portion 41a of the long elastic piece 41 is thrown over the arm and, in such a state, the curled elastic member 1G is uncurled outward at a predetermined angle or more. By the energizing force of the coil spring 50, the curled elastic member 1G naturally enters a maximum uncurled state. When the elastic member 1G is set in a predetermined region of an arm and is curled at a predetermined angle or more, the elastic member 1G is naturally curled by the energizing force of the coil spring 50, and is fit to the arm with a proper pressing force.

As described above, the cuff for the blood pressure monitor of the present invention has the curled elastic member in a peculiar form. Consequently, the cuff can be easily attached to an arm. When the cuff is attached to an arm, the end portions do not easily cut in the flesh of the arm, so that the subject does not feel pain. The shape of the cuff can be altered in correspondence with variations in arms, so that the cuff fits to an arm excellently.

What is claimed is:

1. A cuff for a blood pressure monitor, comprising a bladder and a normally curled elastic member disposed on the outside of the bladder to hold a ring shape of the cuff,
  wherein the normally curled elastic member comprises a material having at least two different rigidities in an axial direction of the ring shape,
  the portion of the normally curled elastic member having the lower rigidity including holes formed therein.

2. The cuff for a blood pressure monitor of claim 1, wherein the cuff is configured to be attached on an arm, and the normally curled elastic member has a higher rigidity of the different rigidities in a portion of the normally curled elastic member that is positioned at a thin portion of the arm when the cuff is attached on the arm and has a lower rigidity of the different rigidities in a portion of the normally curled elastic member that is positioned at a thick portion of the arm when the cuff is attached on the arm.

3. The cuff for a blood pressure monitor of claim 1, wherein the normally curled elastic member has at least two different rigidities also in a circumferential direction of the ring shape.

4. A cuff for a blood pressure monitor, comprising a bladder and a normally curled elastic member disposed on the outside of the bladder to hold a ring shape of the cuff,
   wherein the normally curled elastic member is made of a material having at least two different rigidities in a circumferential direction of the ring shape, and
   wherein the cuff is configured to be attached on an arm, and the normally curled elastic member has a higher rigidity of the different rigidities in a portion of the normally curled elastic member that is positioned at a thin portion of the arm when the cuff is attached on the arm and has a lower rigidity of the different rigidities in a portion of the normally curled elastic member that is positioned at a thick portion of the arm when the cuff is attached on the arm
   the portion of the normally curled elastic member having the lower rigidity including holes formed therein.

5. A cuff for a blood pressure monitor, comprising a bladder and a curled elastic member disposed on the outside of the bladder to hold a ring shape of the cuff,
   wherein the curled elastic member has at least two different rigidities in a circumferential direction of the ring shape,
   wherein the cuff is configured to be attached on an arm, and the curled elastic member has a higher rigidity of the different rigidities in a portion of the curled elastic member that is positioned at a thin portion of the arm when the cuff is attached on the arm and has a lower rigidity of the different rigidities in a portion of the curled elastic member that is positioned at a thick portion of the arm when the cuff is attached on the arm, and
   wherein the curled elastic member has the lower rigidity of the different rigidities at an end portion of the curled elastic member along the circumferential direction, the end portion being configured to be curled inside when the cuff is attached on the arm.

6. The cuff for a blood pressure monitor of claim 1, 2, 3 or 4, wherein the portion of the normally curled elastic member having the higher rigidity is thicker than the portion of the normally curled elastic member having the lower rigidity.

* * * * *